(12) United States Patent
Solomon et al.

(10) Patent No.: US 8,105,594 B2
(45) Date of Patent: Jan. 31, 2012

(54) METHODS FOR AMYLOID REMOVAL USING ANTI-AMYLOID ANTIBODIES

(76) Inventors: Alan Solomon, Knoxville, TN (US); Rudi Hrncic, Knoxville, TN (US); Jonathan Stuart Wall, Knoxville, TN (US)

(*) Notice: Subject to any disclaimer, the term of this patent is extended or adjusted under 35 U.S.C. 154(b) by 0 days.

(21) Appl. No.: 12/693,085

(22) Filed: Jan. 25, 2010

(65) Prior Publication Data
US 2010/0322932 A1 Dec. 23, 2010

Related U.S. Application Data

(63) Continuation of application No. 09/316,387, filed on May 21, 1999, now abandoned.

(60) Provisional application No. 60/086,198, filed on May 21, 1998.

(51) Int. Cl.
*A61K 39/395* (2006.01)

(52) U.S. Cl. ............... 424/135.1; 424/133.1; 424/152.1; 424/172.1

(58) Field of Classification Search .................. None
See application file for complete search history.

(56) References Cited

U.S. PATENT DOCUMENTS

| | | |
|---|---|---|
| 4,666,829 A | 5/1987 | Glenner et al. |
| 4,713,366 A | 12/1987 | Stevens |
| 5,004,697 A | 4/1991 | Pardridge |
| 5,057,540 A | 10/1991 | Kensil et al. |
| 5,187,153 A | 2/1993 | Cordell et al. |
| 5,192,753 A | 3/1993 | McGeer et al. |
| 5,208,036 A | 5/1993 | Eppstein et al. |
| 5,220,013 A | 6/1993 | Ponte et al. |
| 5,231,000 A | 7/1993 | Majocha et al. |
| 5,231,170 A | 7/1993 | Averback |
| 5,270,165 A | 12/1993 | Van Nostrand et al. |
| 5,387,742 A | 2/1995 | Cordell |
| 5,434,170 A | 7/1995 | Andrulis, Jr. |
| 5,441,870 A | 8/1995 | Seubert et al. |
| 5,464,823 A | 11/1995 | Lehrer et al. |
| 5,571,499 A | 11/1996 | Hafler et al. |
| 5,571,500 A | 11/1996 | Hafler et al. |
| 5,583,112 A | 12/1996 | Kensil et al. |
| 5,585,100 A | 12/1996 | Mond et al. |
| 5,593,846 A | 1/1997 | Schenk et al. |
| 5,605,811 A | 2/1997 | Seubert et al. |
| 5,612,486 A | 3/1997 | McConlogue et al. |
| 5,622,701 A | 4/1997 | Berg |
| 5,641,473 A | 6/1997 | Hafler et al. |
| 5,641,474 A | 6/1997 | Hafler et al. |
| 5,645,820 A | 7/1997 | Hafler et al. |
| 5,679,348 A | 10/1997 | Nesburn et al. |
| 5,688,651 A | 11/1997 | Solomon |
| 5,721,130 A | 2/1998 | Seubert et al. |
| 5,733,547 A | 3/1998 | Weiner et al. |
| 5,736,142 A | 4/1998 | Sette et al. |
| 5,744,368 A | 4/1998 | Goldgaber et al. |
| 5,750,349 A | 5/1998 | Suzuki et al. |
| 5,750,361 A | 5/1998 | Prusiner et al. |
| 5,753,624 A | 5/1998 | McMichael et al. |
| 5,776,468 A | 7/1998 | Hauser et al. |
| 5,780,587 A | 7/1998 | Potter |
| 5,786,180 A | 7/1998 | Konig et al. |
| 5,824,322 A | 10/1998 | Balasubramanian |
| 5,837,473 A | 11/1998 | Maggio et al. |
| 5,837,672 A | 11/1998 | Schenk et al. |
| 5,846,533 A | 12/1998 | Prusiner et al. |
| 5,849,298 A | 12/1998 | Weiner et al. |
| 5,851,996 A | 12/1998 | Kline |
| 5,854,204 A | 12/1998 | Findeis et al. |
| 5,869,054 A | 2/1999 | Weiner et al. |
| 5,869,093 A | 2/1999 | Weiner et al. |
| 5,877,399 A | 3/1999 | Hsiao et al. |
| 5,935,927 A | 8/1999 | Vitek et al. |
| 5,955,079 A | 9/1999 | Mond et al. |
| 5,955,317 A | 9/1999 | Suzuki et al. |
| 5,958,883 A | 9/1999 | Snow |
| 5,989,566 A | 11/1999 | Cobb et al. |
| 6,057,367 A | 5/2000 | Stamler et al. |
| 6,114,133 A | 9/2000 | Seubert et al. |
| 6,150,091 A | 11/2000 | Pandolfo et al. |
| 6,170,226 B1 | 1/2001 | Chang |
| 6,262,335 B1 | 7/2001 | Hsiao et al. |
| 6,284,221 B1 | 9/2001 | Schenk et al. |
| 6,284,533 B1 | 9/2001 | Thomas |
| 6,294,171 B2 | 9/2001 | McMichael |
| 6,399,314 B1 | 6/2002 | Krishnamurthy |
| 6,417,178 B1 | 7/2002 | Klunk et al. |

(Continued)

FOREIGN PATENT DOCUMENTS

CA 2332183 A1 5/1996

(Continued)

OTHER PUBLICATIONS

Abe et al., "Production and lmmunodiagnostic Applications of Anti-human Light Chain Monoclonal Antibodies," Am. J. Clin. Pathol. 100(1):67-74 (1993). Aguizzi, et al., Nature, vol. 389, Oct. 1997,795-798.
Akiyama, et al., GLIA, 25:324-331 (1999).
Akiyama, et al., Neurobiology of Aging, 21 (2000) 383-421.
Andersen et al., Neurology, vol. 45, Aug. 1995, 1441-1445.
Ando et al., "Down regulation of a harmful variant protein by replacement of its normal protein," Biochim. Biophys. Acta 1362:39-46 (1997).
Bard, et al., Nature Medicine, vol. 6, No. 8, Aug. 2000, 916-919.
Bauer et al., Federation of European Biochemical Societies, vol. 285, No. 1, 111-114.
Bellottii et al., "Application of Monoclonal Anti-idiotypes in the Study of AL Amyloidosis: Therapeutic Implications," Ren. Fail. 15(3):365-371 (1993).
Bellottii et al., "Use of Anti-Idiotypic Monoclonal Antibody in Studying Amyloidogenic light Chains in Cells, Urine and Fibrils: Pathophysiology and Clinical Implications," Scand. J. Immunol. 36(4):607-615 (1992).

(Continued)

*Primary Examiner* — Daniel E Kolker
*Assistant Examiner* — Gregory S Emch
(74) *Attorney, Agent, or Firm* — Johnson & Associates

(57) ABSTRACT

Methods and related immunoglobulin peptides and fragments thereof are disclosed that enhance the cell-mediated immune response of a patient to deposits of amyloid fibrils. These methods exploit the opsonizing effect of antibodies directed toward amyloid material or its component parts.

14 Claims, 4 Drawing Sheets

U.S. PATENT DOCUMENTS

| | | |
|---|---|---|
| 6,743,427 B1 | 6/2004 | Schenk |
| 6,750,324 B1 | 6/2004 | Schenk et al. |
| 6,761,888 B1 | 7/2004 | Schenk |
| 6,787,138 B1 | 9/2004 | Schenk |
| 6,787,139 B1 | 9/2004 | Schenk |
| 6,787,140 B1 | 9/2004 | Schenk |
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,808,712 B2 | 10/2004 | Schenk |
| 6,838,592 B1 | 1/2005 | Nixon et al. |
| 2001/0018053 A1 | 8/2001 | McMichael |
| 2001/0021769 A1 | 9/2001 | Prusiner |
| 2002/0009445 A1 | 1/2002 | Du et al. |
| 2002/0077288 A1 | 6/2002 | Frangione et al. |
| 2002/0086847 A1 | 7/2002 | Chain |
| 2002/0094335 A1 | 7/2002 | Chalifour et al. |
| 2002/0102261 A1 | 8/2002 | Raso |
| 2002/0132268 A1 | 9/2002 | Chang et al. |
| 2002/0133001 A1 | 9/2002 | Gefter et al. |
| 2002/0136718 A1 | 9/2002 | Raso |
| 2002/0160394 A1 | 10/2002 | Wu |
| 2002/0162129 A1 | 10/2002 | Lannfelt et al. |
| 2002/0168377 A1 | 11/2002 | Schaetzl |
| 2002/0187157 A1 | 12/2002 | Jensen et al. |
| 2002/0197258 A1 | 12/2002 | Ghanbari et al. |
| 2003/0068325 A1 | 4/2003 | Wang |
| 2003/0073655 A1 | 4/2003 | Chain |
| 2003/0147882 A1 | 8/2003 | Solomon et al. |
| 2003/0165496 A1 | 9/2003 | Basi et al. |
| 2004/0071816 A1 | 4/2004 | Rick |
| 2004/0081657 A1 | 4/2004 | Schenk |
| 2004/0087777 A1 | 5/2004 | Basi et al. |
| 2004/0136993 A1 | 7/2004 | Schenk et al. |
| 2004/0146521 A1 | 7/2004 | Schenk et al. |
| 2004/0157779 A1 | 8/2004 | Schenk |
| 2004/0166119 A1 | 8/2004 | Schenk |
| 2004/0170641 A1 | 9/2004 | Schenk |
| 2004/0171815 A1 | 9/2004 | Schenk et al. |
| 2004/0175394 A1 | 9/2004 | Schenk |
| 2004/0219146 A1* | 11/2004 | Schenk ............... 424/141.1 |
| 2004/0228865 A1 | 11/2004 | Schenk |
| 2004/0247590 A1 | 12/2004 | Schenk et al. |
| 2004/0247591 A1 | 12/2004 | Schenk et al. |
| 2004/0265301 A1 | 12/2004 | Schenk et al. |
| 2004/0265308 A1 | 12/2004 | Schenk |

FOREIGN PATENT DOCUMENTS

| | | | |
|---|---|---|---|
| CA | | 2254931 A1 | 12/1997 |
| EP | | 0285159 A1 | 10/1988 |
| EP | | 0451700 A1 | 10/1991 |
| EP | | 0639081 B1 | 11/1993 |
| EP | | 0276723 B1 | 12/1993 |
| EP | | 0613007 A2 | 8/1994 |
| EP | | 0526611 B1 | 1/1995 |
| EP | | 0683234 A1 | 11/1995 |
| EP | | 0440619 B1 | 1/1996 |
| EP | | 0526511 B1 | 5/1997 |
| EP | | 0782859 A1 | 7/1997 |
| EP | | 0783104 A1 | 7/1997 |
| EP | | 0594607 B1 | 8/1997 |
| EP | | 0845270 A1 | 6/1998 |
| EP | | 0863211 A1 | 9/1998 |
| EP | | 0652962 B1 | 12/1998 |
| EP | | 0911035 A2 | 4/1999 |
| EP | | 0911036 A2 | 4/1999 |
| EP | | 0561087 B1 | 8/1999 |
| EP | | 0506785 B1 | 3/2000 |
| EP | | 1172378 A1 | 1/2002 |
| EP | | 0359783 B2 | 4/2002 |
| EP | | 0666080 B1 | 1/2004 |
| EP | | 0868918 B1 | 4/2004 |
| EP | | 0683234 B2 | 6/2007 |
| GB | | 2220211 A | 1/1990 |
| GB | | 2335192 A | 9/1999 |
| WO | WO 88/10120 A1 | | 12/1988 |
| WO | WO 89/01343 A1 | | 2/1989 |
| WO | WO 89/03687 A1 | | 5/1989 |
| WO | WO 89/06242 A1 | | 7/1989 |
| WO | WO 89/06689 A1 | | 7/1989 |
| WO | WO 90/12870 A1 | | 11/1990 |
| WO | WO 90/12871 A1 | | 11/1990 |
| WO | WO 91/08760 A1 | | 6/1991 |
| WO | WO 91/12816 A1 | | 9/1991 |
| WO | WO 91/16819 A1 | | 11/1991 |
| WO | WO 91/19810 A1 | | 12/1991 |
| WO | WO 92/06187 A1 | | 4/1992 |
| WO | WO 92/06708 A1 | | 4/1992 |
| WO | WO 92/13069 A1 | | 8/1992 |
| WO | WO 92/13089 A1 | | 8/1992 |
| WO | WO 93/02189 A1 | | 2/1993 |
| WO | WO 93/04194 A1 | | 3/1993 |
| WO | WO 93/14200 A1 | | 7/1993 |
| WO | WO 93/15760 A1 | | 8/1993 |
| WO | WO 93/16724 A1 | | 9/1993 |
| WO | WO 93/21950 A1 | | 11/1993 |
| WO | WO 94/01772 A1 | | 1/1994 |
| WO | WO 94/03615 A1 | | 2/1994 |
| WO | WO 94/03815 A1 | | 2/1994 |
| WO | WO 94/17197 A1 | | 8/1994 |
| WO | WO 94/22437 A2 | | 10/1994 |
| WO | WO 94/28412 A1 | | 12/1994 |
| WO | WO 95/04151 A2 | | 2/1995 |
| WO | WO 95/05394 A1 | | 2/1995 |
| WO | WO 95/05853 A1 | | 3/1995 |
| WO | WO 95/11008 A2 | | 4/1995 |
| WO | WO 95/11311 A1 | | 4/1995 |
| WO | WO 95/11994 A1 | | 5/1995 |
| WO | WO 95/12815 A1 | | 5/1995 |
| WO | WO 95/31996 A1 | | 11/1995 |
| WO | WO 96/18900 A1 | | 6/1996 |
| WO | WO 96/25435 A1 | | 8/1996 |
| WO | WO 96/28471 A1 | | 9/1996 |
| WO | WO 96/39176 A1 | | 12/1996 |
| WO | WO 97/10505 A1 | | 3/1997 |
| WO | WO 97/17613 A1 | | 5/1997 |
| WO | WO 97/21728 A1 | | 6/1997 |
| WO | WO 98/07850 A2 | | 2/1998 |
| WO | WO 98/44955 A1 | | 10/1998 |
| WO | WO 99/00150 A2 | | 1/1999 |
| WO | WO 99/06066 A2 | | 2/1999 |
| WO | WO 99/06545 A2 | | 2/1999 |
| WO | WO 99/27911 A1 | | 6/1999 |
| WO | WO 99/27944 A1 | | 6/1999 |
| WO | WO 99/27949 A1 | | 6/1999 |
| WO | WO 99/58554 A1 | | 11/1999 |
| WO | WO 99/58564 A1 | | 11/1999 |
| WO | WO 99/60021 A2 | | 11/1999 |
| WO | WO 99/60024 A1 | | 11/1999 |
| WO | WO 00/43039 A1 | | 7/2000 |
| WO | WO 00/43049 A1 | | 7/2000 |
| WO | WO 00/72870 A1 | | 12/2000 |
| WO | WO 00/72876 A2 | | 12/2000 |
| WO | WO 00/72878 A1 | | 12/2000 |
| WO | WO 00/72880 A2 | | 12/2000 |
| WO | WO 00/77178 A1 | | 12/2000 |
| WO | WO 01/39796 A2 | | 6/2001 |
| WO | WO 01/42306 A2 | | 6/2001 |
| WO | WO 01/42308 A2 | | 6/2001 |
| WO | WO 01/62264 A2 | | 8/2001 |
| WO | WO 01/62284 A2 | | 8/2001 |
| WO | WO 01/62601 A1 | | 8/2001 |
| WO | WO 01/62801 A2 | | 8/2001 |
| WO | WO 01/77167 A2 | | 10/2001 |
| WO | WO 01/90182 A2 | | 11/2001 |
| WO | WO 02/03911 A2 | | 1/2002 |
| WO | WO 02/34777 A1 | | 5/2002 |
| WO | WO 02/34878 A2 | | 5/2002 |
| WO | WO 2004/080419 A2 | | 9/2004 |
| WO | WO 2004/108895 A1 | | 12/2004 |
| WO | WO 2006/113347 A2 | | 10/2006 |

OTHER PUBLICATIONS

Benjamini, et al., Immunology a Short Course, Benjamini & Leskowitz Ed., Wiley-Liss, Inc., New York, NY, 49-65, 1991.

Benjamini, et al.,Immunology: a short course, Benjamin & Leskowitz Ed., Wiley-Liss, Inc., New York, NY, p. 142.
Bercovici, et al., Eur. J. Immunol. (1999),29:345-354.
Bickel et al., "Development and in Vitro Characterization of a Cationized Monoclonal Antibody against BetaA4 Protein: A Potential Probe for Alzheimer's Disease," Bioconjugate Chem. 5(2):119-125 (1994).
Bickel et al., "Site Protected, Cationized Monoclonal Antibody Against Beta Amyloid As a Potential Diagnostic Imaging Technique for Alzheimer's Disease," Society for Neuroscience, Abstracts (325. 6) vol. 18, 1992, 764.
Blass, The New England Journal of Medicine, Nov. 25, 1999, 1694-1695.
Bodmer et al., Biochemical and Biophysical Research Communications, vol. 171, No. 2, Sep. 14, 1990, 890-897.
Borchelt et al., Neuron, vol. 19, Oct. 1997, 939-945.
Boris-Lawrie et al., Current Opinion in Genetics and Development, 1993, 3:102-109.
Borrow, et al., J. Mol. Biol. (1992) 225,1075-1093.
Brugge, et al., Neurology, 44, Feb. 1994, 232-238.
Cameron, Molecular Biotechnology, vol. 7, 1997, 253-265.
Caputo et al., Clin. Neuropharm, vol. 15, Suppl. 1, Pt. A., 1992, 414A-415A.
CBER, U.S.F.D.A., Thimerosal in Vaccines, http://www.fda.gov/cber/vaccine/thimerosol.htm, May 28, 2002.
Chao et al., Abstract No. 513.7, Society for Neuroscience, Abstracts, vol. 19, Part 2, Nov. 1993.
Chapman, Nature, vol. 408, 21/28 Dec. 2000, 915-916.
Check, Nature, vol. 422, Mar. 27, 2003, 370-372.
Chem. Abstract Database, 1971 :417711.
Chen et al., Nature, vol. 408, Dec. 2000, 975-979.
Chen et al., Neuroscience Letters, 125:223-226 (1991).
Chen et al., Progress in Brain Research, vol. 117,327-334 (1998).
Chung, et al.,. The Journal of Biological Chemistry, vol. 274, No. 45, Nov. 5, 1999, 32301-32308.
Coloma et al., Pharmaceutical Research, vol. 17, No. 3, 2000, 266-274.
Conway et al., Proc. Natl. Acad. Sci., Jan. 18, 2000, vol. 97, No. 2, 571-576.
Cordell Annu. Rev. Pharmacol. Toxicol. 1994, 34: 69.
Costa et al., Scand. J. Immunol. 38,177-182,1993.
Daly IV et al., Life Sciences, 1998, vol. 63, No. 23. 2121-2131.
Deena Beasley, Alzheimer's Traced to Proteins Caused by Aging, Reuters, The New York Times, Apr. 20, 2001.
Demattos et al., "Peripheral anti-Aβ antibody alters CNS and plasma Aβ clearance and decreases brain Aβ burden in a mouse model of Alzheimer's disease," Proc. Natl. Acad. Sci. 98(15):8850-8855 (published online Jul. 3, 2001).
Dialog/Derwent Abstract, WPI Acc No. 1997-054436/199706.
Diomede, et al., Biochem. J. (1996) 320, 563-570.
Dodart, et al., Trends in Molecular Medicine, vol. 9, No. 3, Mar. 2003, 85-87.
Du et al., Neurology, 57, Sep. (1 of 2) 2001, 801-805.
Duff et al., Nature, vol. 373, Feb. 9, 1995, 476-477.
Dumery et al., Pathol. Biol., 2001: 49: 72-85.
Elan: News, Elan and AHP Provide an Update on the Phase 2A Clinical Trial of AN-1792, Jan. 18, 2002.
Elan: News, Elan and Syeth provide update on status of Alzheimer's collaboration, Mar. 1, 2002.
Elizan et al., Journal of Neurological Sciences, 1983, 59: 341-347.
Falk et al., "The Systemic Amyloidoses", The New England Journal of Medicine, vol. 337, No. 13, Sep. 25, 1997, pp. 898-908.
Felsenstein et al., Neuroscience Letters, 1993, 152: 185-189.
Felsenstein, et al., Alzheimer's and Parkinson's Diseases, 401-409, 1995.
Finch et al., Neurobiol. Aging, 1996, 17(5): 809-815.
Fisher et al., Proc. Natl. Acad. Sci. USA., vol. 88, pp. 1779-1782, Mar. 1991.
Flanders et al., Neurology, 1995, 45: 1561-1569.
Frautschy, et al., Proc. Natl. Acad. Sci USA,vol. 88, 8362-8366, Oct. 1991.
Frenkel et al., Journal of Neuroimmunology 88 (1998) 85-90.
Frenkel et al., Journal of Neuroimmunology 95 (1999) 136-142.
Frenkel et al., Journal of Neuroimmunology, 106 (2000) 23-31.
Frenkel et al., PNAS, 2000, vol. 97, No. 21, 11455-11459.
Frenkel et al., Vaccine, 19 (2001), 2615-2619.
Friedland et al., Annals New York Academy of Sciences, 1997, 242-247.
Friedland et al., Molecular Neurobiology, vol. 9, 1994, 107-113.
Furlan et al., Brain (2003), 126, 285-291.
Gallo et al., "Potential Role of Apolipoprotein-E in Fibrillogenesis," Am. J. Pathol. 145(3):526-530 (1994).
Games et al., Letters to Nature, vol. 373—Feb. 9, 1995, 523-527.
Games, et al., Annals New York Academy of Sciences, 920:274-284 (2000).
Gandy et al., Tips, Mar. 1992, vol. 13, pp. 108-113.
Gardella et al., Biochemical and Biophysical Research Communications, vol. 173, No. 3, 1990, 1292-1298.
Gaskin et al., J. Exp. Med. vol. 177, Apr. 1993, 1181-1186.
Gearing et al., Annals of Neurology, vol. 39, No. 3, 1996, pp. 395-399.
Geddes et al., Neurobiology of Aging, 20 (1999) 75-79.
Gillmore and Hawkins, "Drug Insight: emerging therapies for amyloidosis," Nature Clin. Practice 2(5):263-270 (2006).
Giulian et al., The Journal of Biological Chemistry, vol. 273, No. 45, Nov. 6, 1998, 29719-29726.
Glenn et al., Nature, vol. 391, Feb. 26, 1998, pp. 851.
Glenner et al., Biochemical and Biophysical Research Communications, vol. 120, No. 3, May 16, 1984, pp. 885-890.
Glenner et al., Biochemical and Biophysical Research Communications, vol. 122, No. 3, Aug. 16, 1984, pp. 1131-1135.
Goate et al., Nature, vol. 349, Feb. 21, 1991, 704-706.
Goldfarb et al., Annu. Rev. Med. 1993, 46:57-65.
Goldsteins et al., Proc. Natl. Acad. Sci. USA, vol. 96 3108-3113, Mar. 1999.
Gonzalez-Fernandez et al., Immunology, 1998, 93, 149-153.
Gortner, et al., Outlines of Biochemistry, Third Edition, 322-323, John Wiley & Sons, Inc. New York, 1999.
Gozes et al., Proc. Natl. Acad. Sci. USA, vol. 93, pp. 427-432, Jan. 1996.
Gravina, et al., The American Society for Biochemistry and Molecular Biology, Inc., vol. 270, No. 13, Mar. 31, 1995, 7013-7016.
Grubeck-Loebenstein et al., "Immunization with β-amyloid: could T-cell activation have a harmful effect?" TINS, vol. 23, No. 3, 2000, pp. 11.
Gupta et al., Vaccine, vol. 15, 12/13, pp. 1341-1343, 1997.
Haass et al., Nature, vol. 359, Sep. 24, 1992, 322-325.
Hanan et al., Amyloid: Int. J. Exp. Clin. Invest. 3, 130-133 (1996).
Hanes et al., Advanced Drug Delivery Reviews, 28 (1997) 97-119.
Haqa et al., Brain Research, 601 (1993) 88-94.
Hardy, The Finnish Medical Society DUODECIM, Ann Med 28, 255-258, 1996.
Hardy, TINS, vol. 20, No. 4, 1997, 154-159.
Harigaya et al., Biochemical and Biophysical Research Communications, vol. 211, No. 3, 1995, Jun. 26, 1995, 1015-1022.
Harrington, et al., Biochem. Biophysica Acta, 1158(1993) 120-128.
Hazama, et al., Immunology, 1993, 78, 643-649.
Helmuth, Science, vol. 289, Jul. 21, 2000, 375.
Hilbich, et al., Eur. J. Biochem. 201, 61-69 (1991).
Holmgren et al., Lancet, vol. 341, May 1, 1993, pp. 1113-1116.
Honda, et al., Journal of Clinical Laboratory Analysis 12:172-178 (1998).
Hrncic et al., "Antibody-Mediated Resolution of Ligh Chain-Associated Amyloid Deposits," Am. J. Pathol. 157(4): 1239-1246 (2000).
Hsiao et al., Science, vol. 274, Oct. 4, 1996, 99-102.
Human Immunology and Cancer Program, The University of Tennessee Medical Center/Graduate School of Medicine, Knoxville, 21 pages (publication location and date unknown).
Hyman et al., The New England Journal of Medicine, vol. 33, No. 19, 1283-1284, Nov. 9, 1995.
Hyman, Down Syndrome and Alzheimer Disease, 123-142, Wiley-Liss, Inc.,1992.
Ida, et al., The Journal of Biochemical Chemistry, vol. 271, No. 37, Sep. 13, 1996, pp. 22908-22914.
Ikeda et al., Laboratory Investigation, 1987, vol. 57 No. 4, 446-449.
Itagaki et al., Journal of Neuroimmunology, 24 (1989) 173-182.

Iwatsubo, et al., Neuron, vol. 13, Jul. 1994, 45-53.
Jäger, Clinical Immunolology and Allergology, Meditsina 1:266 (1990).
Jakes, et al., Alzheimer Disease and Associated Disorders, 1995, vol. 9, No. 1, 47-51.
Jansen et al., Immunological Rev. (1982) vol. 62,185-216.
Janus, et al., Nature, vol. 408, Dec. 2000, 979-982.
Jelic et al., Acta Neuroloqica Scandinavica 2003: 107 (Suppl. 179): 83-93.
Jen, et al., Brain Research Protocols, 2 (1997) 23-30.
Joachim et al., American Journal of Pathology, vol. 138, No. 2, Feb. 1991, 373-384.
Jobling et al., Molecular Microbiology (1991) (7), 1755-1767.
Johnson-Wood et al., Proc. Natl. Acad. Sci USA, Feb. 1997, 94, 1550-1555.
Johnstone et al., Biochemical and Biophysical Research Communications 220, 710-718 (1996).
Jorbeck et al., Infection and Immunity, May 1981, 497-502.
Kalaria, Research in Immunology, 1992, 143:637-641.
Kametani et al., "A monoclonal antibody Hy20-54-16-3L to lambda light chain of human immunoglobulin reacts with amyloid in Alzheimer's disease brain," Neurosci. Lett. 117:62-67 (1990).
Katzav-Gozansky, et al., Biotechnol. Appl. Biochem., (1996) 23:227-230.
Kawabata, Nature, vol. 354, Dec. 12, 1991, 476-478.
Kida, et al., Neuroscience Letters, 193 (1995) 105-108.
Kim, et al., Neuroscience Research Communications vol. 2, No. 3, 121-130, 1988.
Kisilevsky, "Anti-Amyloid Drugs—Potential in the Treatment of Diseases Associated with Aging", Drugs & Aging, vol. 8, No. 2, Feb. 1996, pp. 75-83.
Konig, et al., Annals New York Academy of Sciences, vol. 777, Jan. 1996, 344-355.
Kovacs, et al., J. Neurol (2002) 249:1567-1582.
Kowall et al., "An in vivo model for the neurodegenerative effects of beta amyloid and protection by substance P," Proc. Natl. Acad. Sci. USA. Aug. 15, 1991; 88(16):7247-7251.
Kuo et al., "Water-soluble Aβ (N-40, N-42) Oligomers in Normal and Alzheimer Disease Brains," The Journal of Biological Chemistry, vol. 271, No. 8, Feb. 23, 1996, pp. 4077-4081.
Lampert-Etchells et al., Neurodegeneration, vol. 2, pp. 111-121 (1993).
Langer, Science, vol. 249, Sep. 28, 1990, 1527-1533.
Lannfelt et al., Behavioral Brain Research, 57 (1993) 207-213.
Lansbury, Jr., Current Opinion in Chemical Biology, 1997,260-267.
Lee, "Aβ immunization: Moving Aβ peptide from brain to blood", PNAS, vol. 98, No. 16, Jul. 31, 2001, pp. 8931-8932.
Lemere et al., Abstract No. 519.6, Soc. for Neurosciences Abstracts, vol. 25, Parts 1 & 2, 29th Annual Mtg., Oct. 23-28, 1999.
Lemere et al., Annals New York Academy of Sciences, 920, 328-331 (2001).
Li et al., Biochemistry and Molecular Biology International, vol. 43, No. 3, Oct. 1997, 601-611.
Li et al., Laboratory Investigation, 1998, vol. 78, No. 4, pp. 461-469.
Liang et al., Biochemical and Biophysical Research Communications, 219, 962-967 (1996).
Livingston et al,, The Journal of Immunology, 1997, 1383-1392.
Lomakin et al., "Kinetic Theory of fibrillogenesis of Amyloid β-Protein," Proc. Natl. Acad. Sci. USA 94:7942-7947 (1997).
Majocha, et al., The Journal of Nuclear Medicine, vol. 33, No. 12, Dec. 1992, 2184-2189.
Mak et al., Brain Research, 667 (1994) 138-142.
Mann et al., Annals of Neurology, vol. 40, No. 2, Aug. 1996,149-156.
Mann et al., Neuroscience Letters, 196 (1995) 105-108.
Margaret M. Esiri, Trends in Pharmacological Sciences, vol. 22 No. 1, Jan. 2001, 2-3.
Masliah et al., PNAS, Oct. 9, 2001, vol. 98, No. 21, 12245-12250.
Masters et al., Proc. Natl. Acad. Sci USA, vol. 82, Jun. 1985, 4245-4249.
Mattson, Physological Reviews, vol. 77, No. 4, Oct. 1997, 1081-1132.
McGee et al., J. Microencapsulation, 1997. vol. 14, No. 2, 197-210.
McGeer et al., Journal of Neuroscience Research, 31: 428-442 (1992).
McNeal et al., Virology, 243, 158-166 (1998).
Meda et al., Nature, vol. 374, Apr. 13, 1995, 647-650.
Meduzzi et al., Advances in Clinical Pathology, 2004, 4, 77-85.
Mena et al., Acta Neuropathol (1995) 89:50-56.
Miller et al., J. Exp. Med., vol. 174, Oct. 1991, 791-798.
Mizuno et al., Biochemica et Biophysica Acta, 1373 (1998) 119-130.
Moll et al., Journal of Neurology, Neurosurgery, and Psychiatry, 1993; 56:112-115.
Monsonego et al., PNAS, Aug. 28, 2001, vol. 98, No. 18, 10273-10278.
Morgan et al., Nature, vol. 408, Dec. 2000, 983-985.
Mori et al., The Journal of Biological Chemistry, vol. 267, No. 24, Aug. 25, 1992, 17082-17086.
Morris et al., Neurology, Sep. 1969, 39, 1159-1165.
Munch et al., J. Neural. Transm. (2002) 109: 1081-1087.
Munson, Principles of Pharmacology—Basic Concepts & Clinical Applications, Chapman & Hall, 1995, pp. 47-48.
Murphy et al., American Journal of Pathology, vol. 144, No. 5, May 1994, 1082-1088.
Mutschler et al., Drug Actions—Basic Principles and Therapeutic Aspects, Scientific Publishers; 1995, pp. 7, 11, 12.
Nakamura et al., Exp. Anim. 43(5), 711-718, 1995.
Nakamura et al., Journal of Medical Primatology, 1998,27:244-252.
Nakamura et al., Neuroscience Letters, 201 (1995) 151-154.
Nathanson et al., American Journal of Epidemiology, vol. 145, No. 11, 1997, 959-969.
Neiman, Transgenic Research 7, 73-75 (1998).
Newcombe, et al., Biochemica et Biophysica Acta. 104 (1963) 480-486.
Nicoll et al., Nature Medicine, vol. 9, No. 4, Apr. 2003, 448-452.
Noguchi "Theory and Clinical Application of Chimera Antibody and Humanized Antibody," *Journal of Clinical and Experimental Medicine* 167: 457-462 (1993).
Pahla et al., J. Mol. Med (2001) 78:703-707.
Pan et al., β-Amyloid and the BBB, 2002, 609-615.
Pardridge et al., Biochemical and Biophysical Research Communications, vol. 146, No. 1, 1987, Jul. 15, 1987, 307-313.
Paresce et al., Neuron, vol. 17,553-565, Sep. 1996.
Parsons, Peptide Hormones, Jun. 1976, J. Rudinger, Characteristics of the Amino Acids As Components of a Peptide Hormone Sequencein Peptide Hormones, 1-7, edited by Parsons, JA, et al., 1976.
Paul et al., Eur. J. Immunol. 1995,25:3521-3524.
Perutz, et al., PNAS, Apr. 16, 2002, vol. 99, No. 8, 5591-5595.
Peterson, Laboratory of Animal Science, vol. 46, No. 1, Feb. 1996, 8-14.
Philippe, et al., Journal of Neuroscience Research 46:709-719 (1996).
Prieela et al., Abstract No. 120:86406t, Chemical Abstracts, ACS, vol. 120, 1994, 652.
Prusiner et al., Proc. Natl. Acad. Sci. USA, vol. 90, 10608-10612, Nov. 1993.
Quon et al., Nature, vol. 352, Jul. 18, 1991, 239-241.
Rabin, Acta Neurol Scand 1991: 84: 441-444.
Raso, "Immunotherapy of Alzheimer's Disease," Grant Application No: 1 R43 AG15746-01, 25 pages (publication date unknown).
Raso, Immunotherapy Weekly, Abstract, Apr. 2, 1998.
Rogers et al., Proc. Natl. Acad. Sci. USA., vol. 89 (1992) 1-5.
Rohr et al., "Treatment of Crohn's Disease and Ulcerative Colitis with 7S-Immunoglobulin," Lancet 1(8525):170 (1987).
Rossor et al., Annals of the New York Academy of Sciences. vol. 695, 1993, 198-202.
Saido et al., The Journal of Biological Chemistry, 69, No. 21, Issue of May 27, 1994, 15253-15257.
Saido et al., The Journal of Biological Chemistry, vol. No. 33, Nov. 25, 1993, 25239-25243.
Saito et al., Proc. Natl. Acad. Sci USA, vol. 92, Oct. 1995, 10227-10231.
Saitoh et al., Immunological Analysis of Alzheimer's Disease Using Anti-β-Protein Monoclonal Antibodies, 60 (3) 309-320 (1991).
Sasaki et al., Brain Research, 755 (1997) 193-201.

Schehr, "Therapeutic Approaches to Alzheimer's Disease," Bio/Technology, vol. 12, Feb. 1994, pp. 140-144.
Schenk et al., Arch Neurol, vol. 57, Jul. 2000, 934-936.
Schenk et al., DNA and Cell Biology, vol. 20, No. 11, 2001, 679-681.
Schenk et al., Journal of Medicinal Chemistry, vol. 38, No. 21, Oct. 13, 1995, 4141-4154.
Schenk et al., Nature, vol. 400, Jul. 8, 1999, 173-177.
Selkoe, Imaging Alzheimer's Amyloid, Nature Biotechnology, vol. 18, Aug. 2000, 823-824.
Selkoe, Journal of Neuropathology and Experiments, vol. 53, No. 5, Sep. 1994, pp. 438-447.
Selkoe, Nature, vol. 354, Dec. 12, 1991, 432-433.
Selkoe, Neuron, vol. 6, Apr. 1991, 487-498.
Selkoe, Science, vol. 275, Jan. 31, 1997, 630-631.
Selkoe, Scientific American, Nov. 1991, 68-75.
Selkoe, Trends in Cell Biology vol. 8, Nov. 1998, 447-453.
Selkoe, Trends in Neurosciences, vol. 16, No. 10, Oct. 1993, 409-414.
Sette et al., "Disclaimer, Alteration of Immune Response Using Pan Dr-Binding Peptides," Official Gazette, Jul. 29, 1999, 1 page.
Seubert et al., Nature, vol. 359, Sep. 24, 1992, 325-327.
Shalit et al., Journal of Neuroimmunology, 52 (1994) 147-152.
Shenk et al., "Immunization with amyloid-β attenuates Alzheimer-disease-like pathology in the PDAPP mouse," Nature, vol. 400, Jul. 8, 1999, pp. 173-177.
Shiosaka, Neuroscience Research, 13 (1992), 237-255.
Sigmund, Arteriorscler. Thromb. Vasc. Biol. Jun. 2000, 1425-1429.
Sigurdsson et al., Journal of Neuropathology and Experimental Neurology, vol. 59, No. 1, Jan. 2000, 11-17.
Sigurdsson et al., Neuroscience Letters 336 (2003) 185-187.
Sinha et al., Annals New York Academy of Sciences, 920:206-208 (2000).
Sipe, Ann. Rev. Biochem. 1992, 61: 947-975.
Siqurdsson et al., American Journal of Pathology, vol. 161, No. 1, Jul. 2002, 13-17.
Siqurdsson et al., Neurobiology of Aging, 23 (2002) 1001-1008.
Skolnick et al., Trends in Biotech, 18(1), 34-39, 2000.
Small et al., Nat. Rev. Neuroscience, vol. 2, (8):595-598 (2001).
Smits et al., The Veterinary Quarterly, vol. 19, No. 3, Sep. 1997, 101-105.
Solomon et al. Proc. Natl. Acad. Sci. USA, Apr. 1997, vol. 94, 4109-4112.
Solomon et al., Advances in Molecular and Cell Biology, vol. 15A, 1996, 33-45.
Solomon et al., Proc. Natl. Acad. Sci. USA, Jan. 1996, vol. 93, 452-455.
Solomon, "New Approach Towards Fast Induction of Anti β-Amyloid Peptide Immune Response," Dept. of Mol. Microbiology & Biotechnology, Tel-Aviv University, Ramat Aviv, Tel-Aviv, Israel, p. 182 (publication location and date unknown).
Solomon, "Pro-Rx (Protein Therapeutics)," "Pro-Dx, (Protein Diagnostics)," and "BioBank (Human Myeloma and Amyloid Protein, Cell, & Antibody Resource," 5 pages, University of Tennessee Medical Center (publication location and date unknown).
Solomon, et al., "Activity of Monoclonal Antibodies in Prevention of In Vitro Aggregation of Their Antigens," Immunotechnology, vol. 2, No. 4, Nov. 1996, p. 305, Abstract.
Soto et al., Nat. Med. 4(7), 822-826, 1998.
Southwick et al., "Assessment of Amyloid β Protein in Cerebrospinal Fluid as an Aid in the Diagnosis of Alzheimer's Disease," Journal of Neurochemistry, vol. 66, No. 1, 1996, 259-265.
Spooner et al., Vaccine, 21 (2002) 290-297.
St. George-Hyslop et al., Nature, vol. 400, Jul. 8, 1999, 116-117.
Stein et al., The Journal of Neuroscience, Sep. 1, 2002, 22(17):7380-7388.
Stoute et al., The New England Journal of Medicine, Jan. 9, 1997, 86-91.
Sturchler-Pierrat, et al., Proc. Natl. Acad. Sci, USA, Nov. 1997—vol. 94, 13287-13292.
Su et al., Brain Research, 818(1) (1999) 105-117.
Su et al., Journal of Neuroscience Research, 53:177-186 (1998).
Suzuki et al., American Journal of Pathology, vol. 145, No. 2, Aug. 1994, 452-460.
Suzuki et al., Science, vol. 264, May 27, 1994, 1336-1340.
Szendrei et al., International Journal Peptide Protein Research, 47, 1996, 289-296.
Tal et al., Journal of Neuroscience Research 71:286-290 (2003).
Tan et al., Histopathology, 1994, 25:403-414.
Tanaka et al., European Journal of Pharmacology 352 (1998), 135-142.
Tekirian et al., Journal of Neuropathology and Experimental Neurology,vol. 57, No. 1, Jan. 1998, pp. 76-94.
Tennent et al.,. Proc. Natl. Acad. Sci. USA, vol. 92, May 1995, 4299-4303.
The Boston Globe, "Immune cells may promote Alzheimer's, a study finds," Associated Press, Apr. 17, 1994, Wednesday AM cycle.
The New York Times, "Anti-Inflammatory Drugs May Impede Alzheimer's," Feb. 20, 1994.
Thorsett et al., Current Opinion in Chemical Biology, 2000, 4:377-382.
Tjernberg et al., "Arrest of β-Amyloid Fibril Formation by a Pentapeptide Ligand", The Journal of Biological Chemistry, vol. 271, No. 15, Apr. 12, 1996, pp. 8545-8548.
Trieb et al., Immunobiology, vol. 191, No. 2-3, 1994, 114-115.
Tsuzuki et al., Neuroscience Letters 202 (1995) 77-80.
Van Gool et al., Neuroscience Letters 172 (1994) 122-124.
Vehmas et al., DNA and Cell Biology, vol. 20, No. 11, 2001, 713-721.
Walker et al., "Labeling of Cerebral Amyloid in Vivo with a Monoclonal Antibody," J. Neuropath. Exp. Neurol. 53(4):377-383 (1994).
Wall et al., "In vitro immunoglobulin light chain fibrillogenesis," Meth. Enzymol. 309:204-217 (1999).
Wang, et al., The Journal of Biological Chemistry, Dec. 13, 1996, vol. 271, No. 50, pp. 31894-31902.
Weiner et al., Annals of Neurology, vol. 48, No. 4, Oct. 2000, 567-579.
Weiner et al., Annual Rev. Immunol. 1994, 809-837.
Weissmann et al., Current Opinion in Neurobiology 1997, 7:695-700.
Weldon et al., "Neurotoxicity of Aβ Peptide: Confocal Imaging of Cellular Changes Induced by β-Amyloid in Rat CNS in Vivo," Society for Neuroscience Abstracts, vol. 22, Part 1, p. 193, Abs. No. 81.6 (1996).
Wen, Journal of Food and Drug Analysis, 1998, 6(2):465-476.
Wengenack et al., Nature Biotechnology, Aug. 2000, vol. 18, 868-872.
Werbeek et al., AJP Jan. 1994, vol. 144, No. 1, 104-116.
Wisconsin Alumni Research Foundation, Final Report, Contract No. Ph 43-67-684, Jun. 19,1969, 1-130.
Wisniewski et al., Biochemical Society Transactions, (2002) vol. 30, Part 4, 574-578.
Wong et al., Proc. Natl. Acad. Sci. USA 82 (1985) 8729-8732.
Wrightham et al., Blood 69(3):919-23 (1987).
Wu et al., J. Clin. Invest. vol. 100, No. 7, Oct. 1997, 1804-1812.
Yamada et al., "Further Characterization of a Monoclonal Antibody Recognizing Apolipoprotein E Peptides in Amyloid Deposits," Annals Clin. Lab. Sci. 27(4):276-281 (1997).
Yamaguchi et al., Acta Neuropathol. (1998) 95: 217-222.
Yanagisawa et al., Neurolobiology of Aging, 1998, vol. 19, No. 15, 565-567.
Younkin, Nature Medicine, vol. 7, No. 1, Jan. 2001, 18-19.
Yu et al., "Peptide-Antibody Conjugates for Tumour Therapy: A MHC-Class-II-Restricted Tetanus Toxin Peptide Coupled to an Anti-Ig Light Chain Antibody can Induce Cytotoxic Lysis of a Human B-Cell Lymphoma by Specific CD4 T Cells," Int. J. Cancer 56:244-248 (1994).
Bryce, "Examiner's first report on patent application No. 40075/99," 2 pages, Australia patent appl. No. 40075/99, Australia Patent Office, Woden, Australia (mailed Mar. 5, 2002).
Emch, "Office Action Summary," 13 pages, U.S. Appl. No. 09/316,387, United States Patent and Trademark Office, Alexandria, Virginia, USA (mailed Feb. 7, 2008).
Turner, "Office Action Summary," 29 pages, U.S. Appl. No. 09/316,387, United States Patent and Trademark Office, Alexandria, Virginia, USA (mailed Jun. 20, 2005).

Turner, "Office Action Summary," 17 pages, U.S. Appl. No. 09/316,387, United States Patent and Trademark Office, Alexandria, Virginia, USA (mailed Sep. 30, 2003).

Turner, "Office Action Summary," 9 pages, U.S. Appl. No. 09/316,387, United States Patent and Trademark Office, Alexandria, Virginia, USA (mailed Jan. 18, 2001).

Emch, "Office Action Summary," 17 pages, U.S. Appl. No. 09/316,387, United States Patent and Trademark Office, Alexandria, Virginia, USA (mailed Dec. 24, 2008).

Ballard, "Office Action Summary," 15 pages, U.S. Appl, No. 09/316,387, United States Patent and Trademark Office, Alexandria, Virginia, USA (mailed Sep. 10, 2007).

Turner, "Office Action Summary," 35 pages, U.S. Appl. No. 09/316,387, United States Patent and Trademark Office, Alexandria, Virginia, USA (mailed May 9, 2006).

Emch, "Office Action Summary," 12 pages, U.S. Appl. No. 09/316,387, United States Patent and Trademark Office, Alexandria, Virginia, USA (mailed Apr. 23, 2002).

Turner, "Office Action Summary," 22 pages, U.S. Appl. No. 09/316,387, United States Patent and Trademark Office, Alexandria, Virginia, USA (mailed Jun. 14, 2004).

Knudsen, "International Preliminary Examination Report," 8 pages, PCT Appl. No. PCT/US99/11200, European Patent Office, Munich, Germany (completed Jul. 11, 2000).

Knudsen, "Written Opinion," 7 pages, PCT Appl. No. PCT/US99/11200, European Patent Office, Munich, Germany (mailed Feb. 29, 2000).

Gustafsson/Els, "International Search Report," 5 pages, PCT Appl. No. PCT/US99/11200, European Patent Office, Rijswijk, The Netherlands (mailed Oct. 7, 1999).

Tan, Official Action, 3 pages, Canada Patent Appl. No. 2,325,600, Canada Intellectual Property Office, Gatineau, Quebec, Canada (Feb. 11, 2009).

Tan, Official Action, 5 pages, Canada Patent Appl. No. 2,325,600, Canada Intellectual Property Office, Gatineau, Quebec, Canada (Jan. 3, 2008).

"The First Office Action," 4 pages, China Patent Appl. No. 99808844.7, The Patent Office of the State Intellectual Property Office of the People's Republic of China, Beijing, China (Dec. 26, 2003) with English translation.

Knudsen, "Communication pursuant to Article 96(2) EPC,"4 pages, Europe Patent Appl. No. 99923260.6, European Patent Office, Munich, Germany (May 18, 2005).

Knudsen, "Communication pursuant to Article 96(2) EPC,"5 pages, Europe Patent Appl. No. 99923260.6, European Patent Office, Munich, Germany (May 16, 2006).

Knudsen, "Communication pursuant to Article 96(2) EPC,"5 pages, Europe Patent Appl. No. 99923260.6, European Patent Office, Munich, Germany (Sep. 14, 2007).

Knudsen et al., "Summons to attend oral proceedings pursuant to Rule 115(1) EPC,"6 pages, Europe Patent Appl. No. 99923260.6, European Patent Office, Munich, Germany (Sep. 14, 2007).

Knudsen, "Consultation by telephone with the applicant / representative," 1 page, Europe Patent Appl. No. 99923260.6, European Patent Office, Munich, Germany (Apr. 20, 2009).

Strawman Limited, "Notice of opposition to a European patent," 40 pages, Europe Patent Appl. No. 99923260.6, European Patent Office, Munich, Germany (Jan. 21, 2011).

Mihara, Official Action, 5 pages, from Japan Patent appl. No. 2000-549642, Japan Patent Office (Apr. 21, 2009) with 4 page translation.

Yoshigoe, Official Action, 3 pages, from Japan Patent appl. No. 2000-549642, Japan Patent Office (Nov. 24, 2009) with 3 page translation.

Lim, Official Action, 2 pages, from Korea Patent appl. No. 10-2000-7013040, Korea Patent Office (Feb. 28, 2006) with 2 page translation.

"Memo Concerning the Official Action reported in the Covering Letter," Mexican Patent Appln. No. 011348, 1 page, received from foreign patent counsel (Feb. 15, 2006) redacted.

"Memo Concerning the Official Action reported in the Covering Letter," Mexican Patent Appln. No. 011348, 2 pages, received from foreign patent counsel (Sep. 12, 2008) redacted.

"Memo Concerning the Official Action reported in the Covering Letter," Mexican Patent Appln. No. 011348, 1 page, received from foreign patent counsel (Nov. 26, 2009) redacted.

"Memo Concerning the Official Action reported in the Covering Letter," Mexican Patent Appln. No. 011348, 1 page, received from foreign patent counsel (Jul. 27, 2010) redacted.

Girvan, "Examination Report," 2 pages, New Zealand patent appl. No. 507727, Intellectual Property Office of New Zealand (Apr. 22, 2002).

"Official Action" 3 pages, Russia patent appl. No. 2000132207/14, Russian Patent and Trademark Agency (Jan. 8, 2003) with 2 page translation.

Tillott, "Examiner's first report on patent application No. 2003262458," 3 pages, Australia patent appl. No. 2003262458, Australia Patent Office (Sep. 6, 2006).

"Notice on Office Action," 4 pages, China patent appl. No. 200410063651.1, The Patent Office of the State Intellectual Property Office of the People's Republic of China (Nov. 11, 2005) with 6 page translation.

"The Second Office Action," 4 pages, China patent appl. No. 200410063651.1, The Patent Office of the State Intellectual Property Office of the People's Republic of China (Jan. 19, 2007) with 5 page translation.

"The Third Office Action," 3 pages, China patent appl. No. 200410063651.1, The Patent Office of the State Intellectual Property Office of the People's Republic of China (Sep. 12, 2008) with 4 page translation.

"Decision on Rejection," 3 pages, China patent appl. No. 200410063651.1, The Patent Office of the State Intellectual Property Office of the People's Republic of China (Jul. 10, 2009) with 4 page translation.

Official Action, 6 pages, Russia patent appl. No. 2004107695/14, Russian Patent and Trademark Agency (Nov. 29, 2007) with 5 page translation.

Official Action, 7 pages, Russia patent appl. No. 2004107695/14, Russian Patent and Trademark Agency (Jan. 2009) with 5 page translation.

Office Action dated Aug. 1, 2011 for Canadian Patent Application No. 2,325,600.

Office Action dated Sep. 13, 2011 for U.S. Appl. No. 11/911,506.

\* cited by examiner

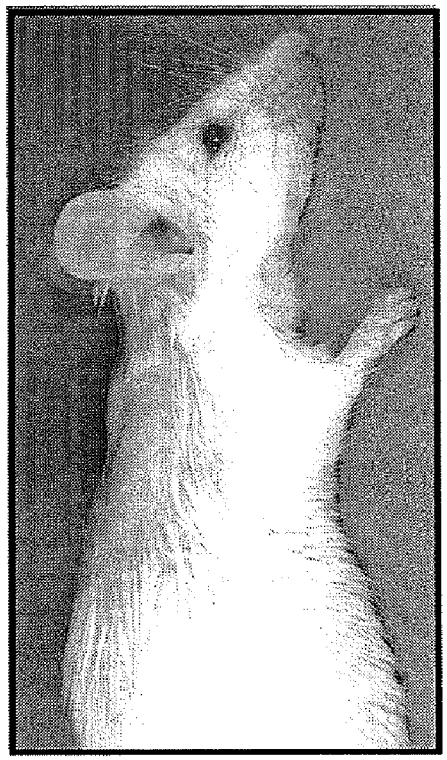
Fig 1B  Day 14 (4)
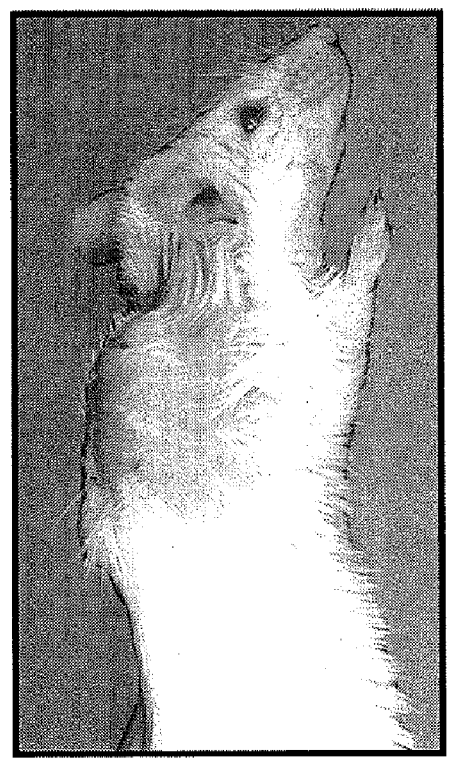
Fig 1A  Day 1 anti-λVIII (31-8C7)

Her

CR anti-κIV (11-1F4)

anti-κI (57-18-H12)

METHODS FOR AMYLOID REMOVAL USING ANTI-AMYLOID ANTIBODIES

CROSS-REFERENCE TO RELATED APPLICATIONS

This Application is a continuation of U.S. Serial No. 09/316,387, filed on May 21, 1999, now abandoned which claims priority to U.S. provisional patent application no. 60/086,198, filed May 21, 1998, each of which is hereby incorporated by reference in its entirety.

FEDERAL SUPPORT

This invention was made with government support under Grant No. 2 R01 CA 20056, awarded by The National Institutes of Health. Thus, the government may have certain rights in this invention.

TECHNICAL FIELD

The present invention generally relates to methods for treating amyloid-related diseases. Specifically, the present invention provides therapeutic antibody-related methods to effect the removal of amyloid fibrils by a patient's own immunophagocytic system.

BACKGROUND OF THE INVENTION

Amyloidosis refers to the pathological deposition of proteins in the form of congophilic, green birefringent fibrils, when congo red-stained, either dispersed or in the form of localized amyloidomas. Such deposits are symptomatic of several diseases, for example Alzheimer's Disease, inflammation-associated amyloid, type II diabetes, bovine spongiform encephalopathy (BSE), Creutzfeld-Jakob disease (CJD), scrapie and primary amyloidosis.

Amyloidoses are generally categorized into three groups: major systemic amyloidoses, major localized amyloidoses, and miscellaneous amyloidoses. Major systemic amyloidoses include: chronic inflammatory conditions (e.g., tuberculosis, osteomyelitis, etc.); non-infectious conditions such as juvenile rheumatoid arthritis, ankylosing spondylitis and Crohn's disease, etc.; familial Mediterranean Fever, plasma cell dyscrasia (primary amyloidosis) and various familial polyneuropathies and cardiomyopathies. Major localized amyloidoses include: chronic dialysis usually for greater than 8 years, Alzheimer's disease, Down syndrome, Hereditary cerebral hemorrhage (Dutch), and non-traumatic cerebral hemorrhage of the elderly. Miscellaneous amyloidoses include: familial polyneuropathy (Iowa), familial amyloidosis (Finnish), hereditary cerebral hemorrhage (Icelandic), CJD, Medullary carcinoma of the thyroid, atrial amyloid, and diabetes mellitus (insulinomas). Other amyloidoses include those referenced in Louis W. Heck, "The Amyloid Diseases" in Cecil's Textbook of Medicine 1504-6 (W.B. Saunders & Co., Philadelphia, Pa.; 1996).

Transmissible spongiform encephalopathies which cause CJD and Gerstmann-Strässler-Scheinker (GSS) disease are described by B. Chesebro et al., "Transmissible Spongiform Encephalopathies: A Brief Introduction" in FIELD'S VIROLOGY 2845-49 (3rd Edition; Raven Publishers, Philadelphia, Pa.; 1996) and in D. C. Gajdusek, "Infectious amyloids: Subacute Spongiform Encephalopathies as Transmissible Cerebral Amyloidoses," 2851-2900 in FIELDS VIROLOGY (1996). Many of these diseases are likely mediated by prions, an infectious protein. See S. B. Prusineri, "Prions" in FIELDS VIROLOGY 2901-50 (1996) and the references contained therein. The inherited forms of amyloidoses as described on Online Mendelian Inheritance in Man (OMIM) "www.ncbi.nlm.nih.gov/htbin-post/Omim/dispmim?" Each of the above is incorporated herein by reference.

Very rarely do patients with clinically proven amyloidosis spontaneously achieve complete remission, perhaps because the amyloid fibrils themselves are non-immunogenic. Various therapies for amyloidosis have been investigated, such as high-dose chemotherapy, steroids, iodinated doxorubicin, and stem cell replacement therapy. However, in only one type of amyloid disease, Familial-Mediterranean amyloidosis, has drug treatment (with colchicine) been shown to be effective.

The use of monoclonal antibodies (mAbs) to induce or modulate the immunological removal of an otherwise unrecognized entity is known. mAbs have been successfully used in treating non-Hodgkins lymphoma and breast cancer, for example.

Previously, a variety of studies have characterized antibodies that bind to amyloid proteins or amyloid fibrils. See, for example, U.S. Pat. Nos. 5,714,471; 5,693,478; 5,688,651; 5,652,092; 5,593,846; 5,536,640; 5,385,915; 5,348,963; 5,270,165; 5,262,332; 5,262,303; 5,164,295; and 4,782,014. In addition, several publications have suggested that anti-amyloid antibodies might be useful for studying the progression of beta-amyloidosis and for various therapeutic options. See, for example, Bellottii et al., Scand. J. Immunol. (1992) 36(4):607-615; Bellotti et al., Ren. Fail. (1993) 15(3):365-371; Walker et al. J. Neuropathol. Exp. Neurol. (1994) 53(4): 377-383; and Bickel et al., Bioconjug. Chem. (1994) 5(2): 119-125. However, no therapeutic antibody has been demonstrated to halt or reverse the deposition of amyloid fibrils in a patient. Thus, a need exists for a method for treating amyloidoses using antibody formulations containing antibodies that bind to amyloid fibrils.

SUMMARY OF THE INVENTION

The present inventors have discovered new methods of treating amyloid-related diseases and conditions. These methods exploit the opsonizing effect of mAbs directed toward the protein constituents of amyloid.

The present invention includes a method of treating a patient having an amyloid-associated disease comprising the step of administering to the patient a therapeutically effective dose of at least one immunoglobulin polypeptide, or fragments thereof, together with a pharmaceutically acceptable carrier; wherein the immunoglobulin polypeptide or fragment thereof, may be a substantially purified immunoglobulin polypeptide that binds to a human amyloid fibril, wherein binding of the polypeptide opsonizes the amyloid fibril.

In particular, the present invention relates to the use of any one of, or a combination of, the three monoclonal antibodies discussed below. These antibodies have general anti-amyloid binding properties and provide an extrinsic opsonizing reagent that activates a patient's own cellular immune clearance mechanism.

BRIEF DESCRIPTION OF THE DRAWINGS

FIGS. 1A and 1B are reproduced photographs of a Balb/c mouse just after an injection of amyloid is made (1A) and 14 days after the injection (1B). The injection site was shaved to better illustrate the "hump" caused by the injection of the amyloid material.

FIG. 3A is a tissue sample from a patient with κ1 amyloidosis stained with Congo red; the amyloid deposits, viewed under polarized light, appear as blue-green particles. FIG. 3B is a tissue sample stained with alkaline phosphatase after labeling with anti-κI (57-18-H12) mAb. FIG. 3C is a tissue sample stained as in FIG. 3B, but with anti-κIV (11-1F4) mAb. FIG. 3D is a tissue sample stained as in FIG. 3B, but with anti-λVIII (31-8c7) mAb.

MODES OF CARRYING OUT THE INVENTION

General Description

Figure 2A:
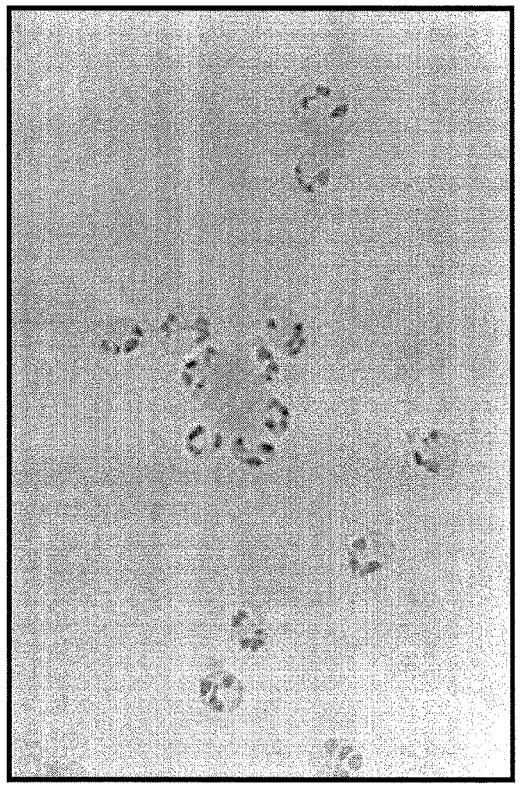
FIGS. 2A and 2B are reproduced photographs of human neutrophils (multi-lobed nuclei) adhering to human amyloid opsonized in vitro.

The present invention utilizes immunoglobulin polypeptides to modulate and to enhance the degradation and removal of undesired deposits of amyloid fibrils in a host or patient. It is envisioned that the invention will be used, for example, to treat humans suffering from a disease or condition characterized by an undesired deposition of amyloid fibrils. Without intending to be bound by any particular mechanism of action, it is believed that the administration of immunoglobulin peptides according to the present invention opsonize the deposited amyloid fibrils in a patient suffering from amyloidosis, thereby assisting in their removal from the patient by the patients' own immune system. It is believed that the patient's immune system alone is unable to remove the amyloid fibrils in conditions modulated by amyloid fibrils without such a therapeutic intervention, presumably because the amyloid fibrils are themselves relatively non-immunogenic.

To treat a patient with amyloidosis, a therapeutically effective dose of immunoglobulin polypeptide or fragment thereof according to the present invention is administered together with a pharmaceutically suitable carrier or excipient. Upon the binding or adhering of such immunoglobulin polypeptides to undesired deposits of amyloid fibrils, the latter are believed to be opsonized.

Single or multiple administrations of the compositions of the present invention can be carried out in dosages and by administration protocols known to those skilled in the art for the administration of other therapeutic antibody products. These parameters may be selected and/or optimized by the physician treating a particular patient.

Preferably, a therapeutically effective dose of a pharmaceutical formulation of the present invention should deliver a quantity of anti-amyloid immunoglobulin polypeptide sufficient to substantially inhibit the undesired deposition of amyloid fibrils or to substantially inhibit the rate of any undesired deposition of amyloid fibrils. More preferably, the formulations should reduce the overall burden of deposited amyloid fibrils in a patient. Further, administration of such formulations should begin shortly after diagnosis of amyloidosis and continue until symptoms are substantially abated and for a period thereafter. In well established cases of disease, loading doses followed by maintenance doses may be required.

Definitions

The terms "peptide," "polypeptide" or "protein" are used interchangeably herein. The term "substantial identity," when referring to polypeptides, indicates that the polypeptide or protein in question is at least about 30% identical to an entire naturally occurring protein or a portion thereof, usually at least about 70% identical, and preferably at least about 95% identical.

As used herein, the terms "isolated," "substantially pure" and "substantially homogenous" are used interchangeably and describe a protein that has been separated from components which naturally accompany it. A substantially purified protein will typically comprise over about 85% to 90% of a protein sample, more usually about 95%, and preferably will be over about 99% pure. Protein purity or homogeneity may be indicated by a number of means well known in the art, such as a polyacrylamide gel electrophoresis of a protein sample, followed by visualizing a single polypeptide band on a polyacrylamide gel upon staining. For certain purposes high resolution will be needed and HPLC or a similar means for purification utilized.

Proteins may be purified to substantial homogeneity by standard techniques well known in the art, including selective precipitation with such substances as ammonium sulfate, column chromatography, immunopurification methods, and others. See, for instance, Scopes, *Protein Purification: Principles and Practice*, Springer-Verlag: New York (1982), which is incorporated herein by reference.

Antibody purification techniques are well known in the art. Harlow et al., *Antibodies: A Laboratory Manual*, Cold Spring Harbor Laboratory Press, Cold Spring Harbor (1988), 288-318, which is incorporated herein by reference, describes, for example, purification using ammonium sulfate precipitation, caprlic acid, DEAE, hydroxyapatite chromatography, gel filtration chromatography, protein A beads, and immunoaffinity.

Nucleic acids, as used herein, may be DNA or RNA. When referring to nucleic acids, the term "substantial identity" indicates that the sequences of two nucleic acids, or designated portions thereof, when optimally aligned and compared, are identical, with appropriate nucleotide insertions or deletions, in at least about 80% of the nucleotides, usually at least about 90% to 95%, and more preferably at least about 98% to 99.5% of the nucleotides.

Alternatively, substantial nucleic acid sequence identity exists when a nucleic acid segment will hybridize under selective hybridization conditions, to a complement of another nucleic acid strand.

"Substantially complementary" similarly means that one nucleic acid hybridizes selectively to, or is identical to, another nucleic acid. Typically, selective hybridization will occur when there is at least about 55% identity over a stretch of at least 14-25 nucleotides, preferably at least about 65% identity, more preferably at least about 75%, and most preferably at least about 90% identity. See M. Kanehisa *Nucleic Acids Res.* 12:203 (1984), which is incorporated herein by reference.

Stringent hybridization conditions will typically include salt concentrations of less than about 1 M, more usually less than about 500 mM and preferably less than about 200 mM. Temperature conditions will typically be greater than 22° C., typically greater than about 30° C. and preferably in excess of about 37° C. As other factors may dramatically affect the stringency of hybridization, including base composition and size of the complementary strands, presence of organic solvents and extent of base mismatching, the combination of parameters is more important than the absolute measure of any one alone.

"Isolated" or "substantially pure," when referring to nucleic acids, refer to those that have been purified away from other cellular components or other contaminants, e.g., other cellular nucleic acids or proteins, by standard techniques, including alkaline/SDS treatment, CsCl banding, column chromatography, and others well known in the art. See, F. Ausubel, et al., ed. *Current Protocols in Molecular Biology*, Greene Publishing and Wiley-Interscience, New York (1987), incorporated herein by reference.

A nucleic acid is "operably linked" when it is placed into a functional relationship with another nucleic acid sequence. For instance, a promoter or enhancer is operably linked to a coding sequence if it affects the transcription of the sequence. Generally, operably linked means that the nucleic acid sequences being linked are contiguous and, where necessary to join two protein coding regions, contiguous and in reading frame.

Techniques for nucleic acid manipulation, such as subcloning nucleic acid sequences encoding polypeptides into expression vectors, labelling probes, DNA hybridization, and so on are described generally, for example in Sambrook et al., (1989) *Molecular Cloning: A Laboratory Manual* (2nd ed.), Vols. 1-3, Cold Spring Harbor Laboratory, or Ausubel et al., ed. (1987) op. cit., both of which are incorporated herein by reference.

"Expression vectors," "cloning vectors," or "vectors" are often plasmids or other nucleic acid molecules that are able to replicate in a chosen host cell. Expression vectors may replicate autonomously, or they may replicate by being inserted into a genome of the host cell, by methods well known in the art. Vectors that replicate autonomously will have an origin of replication or autonomous replicating sequence ("ARS") that is functional in the chosen host cell(s). Often, it is desirable for a vector to be usable in more than one host cell, e.g., in *E. coli* for cloning and construction, and in a mammalian cell for expression.

Mammalian cell lines are often used as host cells for the expression of polypeptides derived from eukaryotes. Propagation of mammalian cells in culture is per se well known. See, *Tissue Culture*, Academic Press, Kruse and Patterson, ed. (1973), incorporated herein by reference. Host cell lines may also include such organisms as bacteria (e.g., *E. coli* or *B. subtilis*), yeast, filamentous fungi, plant cells, or insect cells, among others.

"Transformation" refers to the introduction of vectors containing the nucleic acids of interest directly into host cells by well-known methods. Transformation methods, which vary depending on the type of host cell, include electroporation; transfection employing calcium chloride, rubidium chloride calcium phosphate, DEAE-dextran, or other substances; microprojectile bombardment; lipofection; infection (where the vector is an infectious agent); and other methods. See generally, Sambrook et al., (1989) op. cit. Reference to cells into which the nucleic acids described above have been introduced is meant to also include the progeny of such cells.

As used herein, "immunoglobulin polypeptide" refers to molecules that are derived from native immunoglobulins (e.g., antibodies) that have specific immunoreactive activity against a particular target, e.g., against amyloid fibrils. Antibodies are typically tetramers of immunoglobulin polypeptides. As used herein, the term "antibody" also refers to a protein consisting of one or more polypeptides substantially encoded by immunoglobulin genes. Immunoglobulin genes include those coding for the light chains, which may be of the kappa or lambda types, and those coding for the heavy chains. Heavy chain types are alpha, gamma, delta, epsilon and mu. The carboxy terminal portions of immunoglobulin heavy and light chains are constant regions, while the amino terminal portions are encoded by the myriad immunoglobulin variable region genes. The variable regions of an immunoglobulin are the portions that provide antigen recognition specificity. In particular, the specificity resides in the complementarity determining regions ("CDRs"), also known as hypervariable regions, of the immunoglobulins.

The immunoglobulins may exist in a variety of fragment forms including, for example, Fv, Fab, F(ab'), F(ab')$_2$, ScFv and other fragments, as well as single chains (e.g., Huston, et al., Proc. Nat. Acad. Sci. U.S.A., 85:5879-5883 (1988) and Bird, et al., Science 242:423-426 (1988), which are incorporated herein by reference). (See, generally, Hood, et al., "Immunology," Benjamin, N.Y., 2nd ed. (1984), and Hunkapiller and Hood, *Nature*, 323:15-16 (1986), which are incorporated herein by reference). Single-chain antibodies, in which genes for a heavy chain and a light chain are combined into a single coding sequence, may also be used. Immunoglobulin polypeptide also encompasses a truncated immunoglobulin chain, for example, a chain containing less constant region domains than in the native polypeptide. Such truncated polypeptides can be produced by standard methods such as introducing a stop codon into the gene sequence 5' of the domain sequences to be deleted. The truncated polypeptides can then be assembled into truncated antibodies. Antibodies as used herein also include bispecific antibodies which can be produced such as by the methods described in the following references: Glennie et al., *J. Immunol.*, 139:2367-2375 (1987); Segal et al., *Biologic Therapy of Cancer Therapy of Cancer Updates* 2(4):1-12 (1992); and Shalaby et al., *J. Exp. Med.* 175:217-225 (1992).

"Monoclonal antibodies" may be obtained by various techniques familiar to those skilled in the art. Briefly, spleen cells from an animal immunized with a desired antigen are immortalized, commonly by fusion with a myeloma cell (see, Kohler and Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

Monospecific and bispecific immunoglobulins may also be produced by recombinant techniques in prokaryotic or eukaryotic host cells.

"Chimeric" antibodies are encoded by immunoglobulin genes that have been genetically engineered so that the light and heavy chain genes are composed of immunoglobulin gene segments belonging to different species. For example, the variable (V) segments of the genes from a mouse monoclonal antibody may be joined to human constant (C) segments. Such a chimeric antibody is likely to be less antigenic to a human than antibodies with mouse constant regions as well as mouse variable regions.

As used herein, the term chimeric antibody also refers to an antibody that includes an immunoglobulin that has a human-like framework and in which any constant region present has at least about 85%-90%, and preferably about 95% polypeptide sequence identity to a human immunoglobulin constant region, a so-called "humanized" immunoglobulin (see, for example, PCT Publication WO 90/07861, which is incorporated herein by reference). Hence, all parts of such a "humanized" immunoglobulin, except possibly the complementarity determining regions (CDRs), are substantially identical to corresponding parts of one or more native human immunoglobulin sequences. Where necessary, framework residues may also be replaced with those within or across species especially if certain framework residues are found to affect the structure of the CDRs. A chimeric antibody may also contain truncated variable or constant regions.

The term "framework region," as used herein, refers to those portions of immunoglobulin light and heavy chain variable regions that are relatively conserved (i.e., other than the CDRs) among different immunoglobulins in a single species, as defined by Kabat, et al., (1987); *Sequences of Proteins of Immunologic Interest,* 4th Ed., U.S. Dept. Health and Human Services, which is incorporated herein by reference). As used herein, a "human-like framework region" is a framework region that in each existing chain comprises at least about 70 or more amino acid residues, typically 75 to 85 or more residues, identical to those in a human immunoglobulin.

Human constant region DNA sequences can be isolated in accordance with well-known procedures from a variety of human cells, but preferably from immortalized B-cells. The variable regions or CDRs for producing the chimeric immunoglobulins of the present invention may be similarly derived from monoclonal antibodies capable of binding to the human type amyloid, and will be produced in any convenient mammalian system, including mice, rats, rabbits, human cell lines, or other vertebrates capable of producing antibodies by well-known methods. Variable regions or CDRs may be produced synthetically, by standard recombinant methods, including polymerase chain reaction ("PER") or through phage-display libraries. For phage display methods, see for example, McCafferty et al., *Nature* 348:552-554 (1990); Clackson et al., *Nature* 352:624-628 and Marks et al., *Biotechnology* 11:1145-1149 (1993). Suitable prokaryotic systems such as bacteria, yeast and phage may be employed.

Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A., which is incorporated herein by reference).

In addition to the chimeric and "humanized" immunoglobulins specifically described herein, other substantially identical modified immunoglobulins can be readily designed and manufactured utilizing various recombinant DNA techniques well known to those skilled in the art. In general, modifications of the genes may be readily accomplished by a variety of well-known techniques, such as PCR and site-directed mutagenesis (see, Gillman and Smith, *Gene* 8:81-97 (1979) and S. Roberts et al., *Nature* 328:731-734 (1987), both of which are incorporated herein by reference).

Alternatively, polypeptide fragments comprising only a portion of the primary immunoglobulin structure may be produced. For example, it may be desirable to produce immunoglobulin polypeptide fragments that possess one or more immunoglobulin activities in addition to, or other than, antigen recognition (e.g., complement fixation).

Immunoglobulin genes, in whole or in part, may also be combined with functional regions from other genes (e.g., enzymes), or with other molecules such as toxins, labels and targeting moieties to produce fusion proteins (e.g., "immunotoxins") having novel properties. In these cases of gene fusion, the two components are present within the same polypeptide chain. Alternatively, the immunoglobulin or fragment thereof may be chemically bonded to the toxin or label by any of a variety of well-known chemical procedures. For example, when the label or cytotoxic agent is a protein and the second component is an intact immunoglobulin, the linkage may be by way of heterobifunctional cross-linkers, e.g., SPDP, carbodiimide, glutaraldehyde, or the like.

Suitable labels include, for example, radionuclides, enzymes, substrates, cofactors, inhibitors, fluorescers, chemiluminescers, magnetic particles. See, for examples of patents teaching the use of such labels, U.S. Pat. Nos. 3,817, 837; 3,850,752; 3,939,350; 3,996,345; 4,277,437; 4,275,149; and 4,366,241, all of which are incorporated by reference.

Immunotoxins, including single chain molecules, may also be produced by recombinant means. Production of various immunotoxins is well-known with the art, and methods can be found, for example in "Monoclonal Antibody-Toxin Conjugates: Aiming the Magic Bullet," Thorpe et al., *Monoclonal Antibodies in Clinical Medicine*, Academic Press, pp. 168-190 (1982); E. Vitetta, *Science* (1987) 238:1098-1104; and G. Winter and C. Milstein, *Nature* (1991) 349:293-299; all incorporated herein by reference.

Additional techniques for preparing immunoglobulins and immunoglobulin fragments are described in V. S. Malik et al., *Antibody Techniques*(Academic Press, 1994); C. A. K. Borrebaeck, *Antibody Engineering: Breakthroughs in Molecular Biology* (Oxford Univ. Press, 1995); and P. J. Delves et al., *Antibody Production: Essential Techniques* (John Wiley & Sons, 1997), which are incorporated herein by reference.

"Opsonize", as used herein, refers to the binding of an immunoglobulin polypeptide to a particular target, particularly epitopes found on deposits of amyloid fibrils, such that the antibody and targets together are recognized as "foreign" by the host's cellular immune system. In other words the binding of the immunoglobulin of the present invention enhances the phagocytization of the amyloid fibrils.

"Amyloidosis", as used herein, is intended to refer to any condition that is characterized by the presence of amyloid material. Such material may be in the form of an amyloidoma or more disperse amyloid deposits or fibrils.

Pharmaceutical Compositions

The pharmaceutical compositions for therapeutic treatment according to the present invention are intended for parenteral, oral or local administration. Preferably, the pharmaceutical compositions are administered parenterally, e.g., intravenously, subcutaneously, intradermally, or intramuscularly. As the blood brain barrier is impermeable to IgG (see U. Bickel et al., 1994 Bioconjug. Chem. 5: 119-25), delivery of antibodies to overcome the blood-brain barrier (BBB) may be achieved through liposomal or micellar delivery of the antibody to the desired site. Alternatively, the agents of this invention can be delivered directly into the cerebrospinal fluid (see for example L. C. Walker et al., 1994 J. Neuropathol. Exp. Neurol. 53: 377-83). For other delivery mechanisms, refer to P. M. Friden, 1996 U.S. Pat. No. 5,527,527 and W. M. Pardridge, 1991 U.S. Pat. No. 5,004,697. All of the above documents are incorporated herein by reference.

Thus, the invention provides compositions for parenteral administration which comprise a solution of the anti-amyloid immunoglobulin polypeptide dissolved or suspended in a pharmaceutically acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of anti-amyloid immunoglobulin polypeptides of the invention in the pharmaceutical formulations can vary widely, i.e., from less than about 1%, usually at or at least about 10-15% to as much as 50% or more by weight, and will be selected primarily by fluid volumes, viscosities, etc., in an accordance with the particular mode of administration selected.

Without undue experimentation, one of ordinary skill in the art could determine the quantity of immunoglobulin polypeptides that would be effective in adequately opsonizing an amyloidoma. Amounts effective for this use will depend on, e.g., the nature of the anti-amyloid immunoglobulin polypeptide composition, the manner of administration, the stage and severity of the disease being treated, the weight and general state of health of the patient, and the judgment of the prescribing physician. A typical single dose of 0.5 mg/kg could generally be used. It must be kept in an mind that the anti-amyloid immunoglobulin polypeptide and peptide compositions derived therefrom may be employed in serious disease states, that is, life-threatening or potentially life-threatening situations. In such cases it is possible and may be felt desirable by the treating physician to administer substantial excesses of these compositions. Thus, human anti-amyloid monoclonal antibodies or substantially human anti-amyloid receptor monoclonal antibodies of the invention are most preferred under these circumstances.

Treatment of humans with amyloidosis according to the present invention could also be applied to animals susceptible to amyloidosis, such as cows or chickens. Thus, references to human patients herein apply also to non-human patients.

The immunoglobulin polypeptides, as defined herein, are preferably anti-amyloid mAbs directed toward an amyloidoma or components or precursors thereof. The mAbs can be raised against IgLC variable region domains or, preferably, against the IgLC subsets κ1, κ4, λ8, or combinations thereof. The administration to humans of immunoglobulin polypeptides that are substantially non-human may elicit anti-antibody responses. Thus, it may be desirable to prepare anti-IgLC immunoglobulin polypeptides of the present invention which are substantially human. By "substantially human" is meant an antibody or binding fragment thereof comprised of amino acid sequences which are at least about 50% human in origin, at least 70 to 80% more preferred, and about 95-99% or more human most preferred, particularly for repeated administrations over a prolonged period as may be necessary to treat established cases of amyloidosis. As used herein, human antibody is meant to include antibodies of entirely human origin as well as those which are substantially human, unless the context indicates otherwise.

Monoclonal antibodies can also be raised against synthetic amyloid fibrils. Recombinant light chain, variable region peptides are isolated and purified in vitro using standard techniques. Synthetic fibrils are then prepared from the peptides using techniques such as those described by Wall et al., "In vitro Immunoglobulin Light Chain Fibrillogenesis," METHODS IN ENZYMOLOGY, Vol. 309 (In Press). Antibodies are then raised against the synthetic fibrils using standard immunization techniques, typically in mice or rabbits. Monoclonal cell lines secreting anti-fibril antibodies are produced using standard hybridoma techniques.

The anti-amyloid immunoglobulin polypeptides of the invention may be prepared by any of a number of well-known techniques. For instance, they may be prepared by immunizing an animal with purified or partially purified human amyloid. The animals immunized can be any one of a variety of species which are capable of immunologically recognizing epitopes characteristic of the human type amyloid extracellular domain, such as murine, lagomorph, equine, etc.

Monoclonal antibodies of the invention may be prepared by immortalizing cells comprising nucleic acid sequences which encode immunoglobulin polypeptides or portions thereof that bind specifically to antigenic determinants characteristic of the extracellular domain of the human type amyloid. The immortalization process can be carried out by hybridoma fusion techniques, by viral transformation of antibody-producing lymphocytes, recombinant DNA techniques, or by techniques that combine cell fusion, viral transformation and/or recombinant DNA methodologies. Immunogens to raise the monoclonal antibodies include synthetic amyloid fibrils as described, for example by, A. Lomakin et al., 1997 Proc. Nat'l Acad. Sci. USA 94: 7942-7, which is incorporated herein by reference.

As the generation of human anti-amyloid monoclonal antibodies may be difficult with conventional immortalization techniques, it may be desirable to first make non-human antibodies and then transfer via recombinant DNA techniques the antigen binding regions of the non-human antibodies, e.g., the Fab, complementarity determining regions (CDRs) or hypervariable regions, to human constant regions (Fc) or framework regions as appropriate to produce substantially human molecules. Such methods are generally known in the art and are described in, for example, U.S. Pat. No. 4,816,397, PCT publication WO 90/07861, and EP publications 173494 and 239400, wherein each is incorporated herein by reference. However, completely human antibodies can be produced in transgenic animals. The desired human immunoglobulin genes or gene segments can be isolated, for example by PCR from human B cells, the DNA cloned into appropriate vectors for expression in eukaryotic cells and the cloned DNA introduced into animals to produce transgenics. Animals suitable for the production of transgenics expressing human immunoglobulin include mice, rats, rabbits and pigs with rodents of transgenics that express human immunoglobulins should preferably have one or more of their endogenous immunoglobulin loci inactivated or "knocked-out" to facilitate identification and isolation of the human antibodies (See e.g., Lonberg, et al. Nature 368:856-859 (1994)).

The resulting chimeric antibodies or chimeric immunoglobulin polypeptides that bind to human amyloid are also within the scope of the present invention. A typical therapeutic chimeric antibody would be a hybrid protein consisting of the variable (V) or antigen-binding domain from a mouse immunoglobulin specific for a human amyloid antigenic determinant, and the constant (C) or effector domain from a human immunoglobulin, although domains from other mammalian species may be used for both variable and constant domains. As used herein, the therm "chimeric antibody" also refers to antibodies coded for by immunoglobulin genes in which only the CDRs are transferred from the immunoglobulin that specifically recognizes the antigenic determinants, the remainder of the immunoglobulin gene being derived from a human (or other mammalian, as desired) immunoglobulin gene. As discussed before, this type of chimeric antibody is referred to as a "humanized" (in the case of a human immunoglobulin gene being used) antibody. Also considered are recombinant human antibodies that do not contain sequences of another species.

The hypervariable regions of the variable domains of the anti-amyloid immunoglobulin polypeptides comprise a related aspect of the invention. The hypervariable regions, or CDRs, in conjunction with the framework regions (those portions of immunoglobulin light and heavy chain variable regions that are relatively conserved among different immunoglobulins in a single species), enable the anti-amyloid immunoglobulin polypeptides to recognize and thus bind to human amyloid. The hypervariable regions can be cloned and sequenced. Once identified, these regions that confer specific recognition of human amyloid can then be cloned into a vector for expression in a host as part of another immunoglobulin molecule or as a fusion protein, e.g., a carrier molecule which functions to enhance immunogenicity of the cloned idiotype.

The anti-amyloid immunoglobulin polypeptides of the invention will generally be used intact, or as immunogenic fragments, such Fv, Fab, F(ab')$_2$ fragments. The fragments may be obtained from antibodies by conventional techniques, such as by proteolytic digestion of the antibody using, e.g., pepsin, papain or other proteolytic enzymes, or by recombinant DNA techniques in which a gene or portion thereof encoding the desired fragment is cloned or synthesized, and expressed in a variety of hosts.

Those skilled in the art will realize that "anti-idiotypic" antibodies can be produced by using a specific immunoglobulin as an immunogen in accordance with standard techniques. For example, infection or immunization with an amyloid fibril or fragment thereof, induces a neutralizing immunoglobulin, which has on its Fab variable region combining site an image of the amyloid that is unique to that particular immunoglobulin, i.e., an idiotype. Immunization with such an anti-amyloid immunoglobulin induces an anti-idiotype antibody, which has a conformation at its combining site that mimics the structure of the original amyloid antigen. These anti-idiotype antibodies may therefore be used instead of the amyloid antigen. See, for example, Nisonoff (1991) *J. Immunol.* 147:2429-2438, which is incorporated herein by reference.

The following working examples specifically point out preferred embodiments of the present invention, and are not to be construed as limiting in any way the remainder of the disclosure. Other generic configurations will be apparent to one skilled in the art.

EXAMPLE 1

Unassisted Resolution of Human IgLC Amyloid in Murine Host

Human IgLC amyloid was extracted and purified from infected organs obtained during an autopsy. The first experiments involved transplanting 50-200 mg of this amyloid material into a Balb/c mouse. The amyloid mass, or "amyloidoma," was prepared in sterile PBS by serial sonication and grinding steps in order to produce a fine suspension of amyloid fibrils complete with the accessory molecules found in vivo. This procedure was performed to allow the amyloid to be injected into the mice through a wide-gauge hypodermic needle.

The amyloid material, equivalent to 10% of the body weight of the animal, was injected into mice (under anesthetic) between the scapula, which resulted in a large mass being visible (see FIG. 1A). The mouse required 15-18 days to achieve the complete removal of the amyloidoma (see FIG. 1B), after which the animal appeared healthy and lived a normal life span. The removal of the amyloidoma was determined subjectively by the experimenter; by simply palpating the injection site, an amyloidoma, like a hard pea, can be easily felt under the skin.

EXAMPLE 2

Involvement of Both Antibody-Mediated and Cellular Immunity in the Removal of Amyloidomas The involvement of anti-amyloid antibodies in the removal of amyloidomas was shown by screening serum from a mouse previously injected with amyloid material against a sample of the injected material. This was done by Western blot analysis using suitable dilutions of the mouse serum as the primary antibody. It was shown that there were antibodies to every component of the amyloid matrix, i.e., every band on the gel was stained by the mouse serum, even at a 10,000-fold serum dilution (data not shown).

Figure 2B:
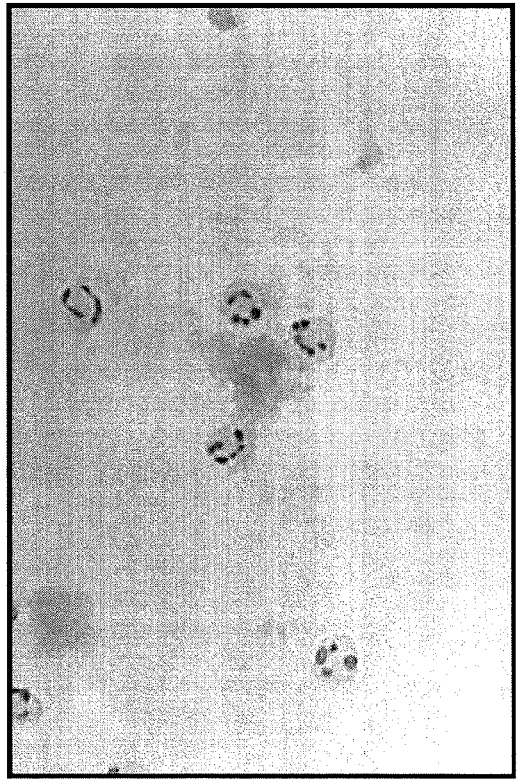
Figure 3D:
FIGS. 3A-3D are reproduced photographs of immunohistochemically stained amyloid-laden tissue samples (20× magnification).
Figure 3A:
Figure 3C:
Figure 3B:

The involvement of a cellular component was demonstrated by in vitro neutrophil binding assays (see FIGS. 2A and 2B) and by using knockout-mutant mouse strains (data not shown). FIGS. 2A and 2B show human neutrophils adhering to human amyloid after the amyloid was treated with mouse anti-human IgLC mAbs. This shows that the mouse mAb can bind to human amyloid as well as attract human neutrophils.

Studies of knockout-mutant mouse strains further support a finding of antibody involvement in amyloid removal. First, scid/scid mice, which lack B and T lymphocytes, were unable to remove an injected amyloidoma even after three months (data not shown). Second, CD 18 knockout animals were unable to remove the amyloidoma as rapidly as normal animals. CD18 knockout animals are 97% deficient in CD18, a cell surface integrin found on granulocyte/macrophage lineages. Although these cells cannot leave the circulation, the animals are B and T cell competent and can therefore mount an antibody response. Third, nude mice, which have no white blood cells, were unable to remove the amyloidoma.

Furthermore, amyloid that had been incubated with amyloid-reactive serum from another mouse, when implanted into the second mouse, was removed within 4 days. In this experiment a Balb/c mouse was injected with 50 mg HIG amyloid and left for 1 week, after which it was bled by tail-vein clipping. The blood was spun down at 1500 rpm and the cells removed by aspiration. The plasma was stored at 4° C. until used. Another preparation of HIG amyloid (100 mg) was prepared by suspending in sterile PBS to which was added 1 ml of plasma from the previous mouse. This preparation was then injected into a second mouse (Balb/c) and the amyloid was removed in 4 days. Thus, it was concluded that the process could be sped up by opsonizing the material prior to injection.

EXAMPLE 3

ELISA Screening of IgLC Subsets

A systematic study was performed using ELISA techniques to screen a large number of human extracted amyloid samples using mAbs raised against the IgLC subsets (λ1, λ2, λ3, λ4, λ5, λ6, κ1, κ2, κ3, κ4, free κ and λ and total κ and λ). Interestingly, it was found that more often than not, the amyloids tested positive with mAbs specific for their own subtype, the total κ or λ antibodies and a κ1 (57-18H12), κ4 (11-1F4) and λ8(31-8C7) mAb. These latter three reagents were found to react in a non-subgroup specific manner, i.e., κ1 reacted with amyloids comprised of IgLCs other than κ1;

and the other two mAbs exhibit the same quality. This shows that the epitope recognized by these antibodies may be a general feature of amyloid fibrils, indicating the possibility of a shared amyloid epitope that can be targeted.

EXAMPLE 4

Immunochemical Staining

Tissue samples from amyloid patients were stained using standard immunochemical techniques and a similar binding phenomenon was observed. FIGS. 3A-3D show that anti-κ1 binds to the κ1 amyloid and, surprisingly, that the anti-κ4 reacts with the κ1 amyloid, suggesting an amyloid epitope that these antibodies may recognize. Additionally, the anti-κ4 reacts with λ-containing amyloid (not illustrated). This is an example of cross-isotype reactivity. However, the results from the ELISA and the immunohistochemistry were not always consistent. This is likely due to the inherent difference in what you are looking at, i.e., ELISA is a liquid phase binding assay using extracted purified amyloid, whereas immunohistochemistry is performed on fixed tissue sections on a slide.

Samples of hybridoma cells that secrete anti-κ1(57-18-H12 (ATCC Acc. No. PTA-104)), anti-κ4(11-IF4(ATCC Acc. PTA-105)) and anti-λ8(31-8c7 (ATCC Acc. No. PTA-103)) monoclonal antibodies were deposited with the American Type Culture Collection (ATCC) on May 21, 1999 in compliance with the Budapest Treaty.

EXAMPLE 5

Figure 4:
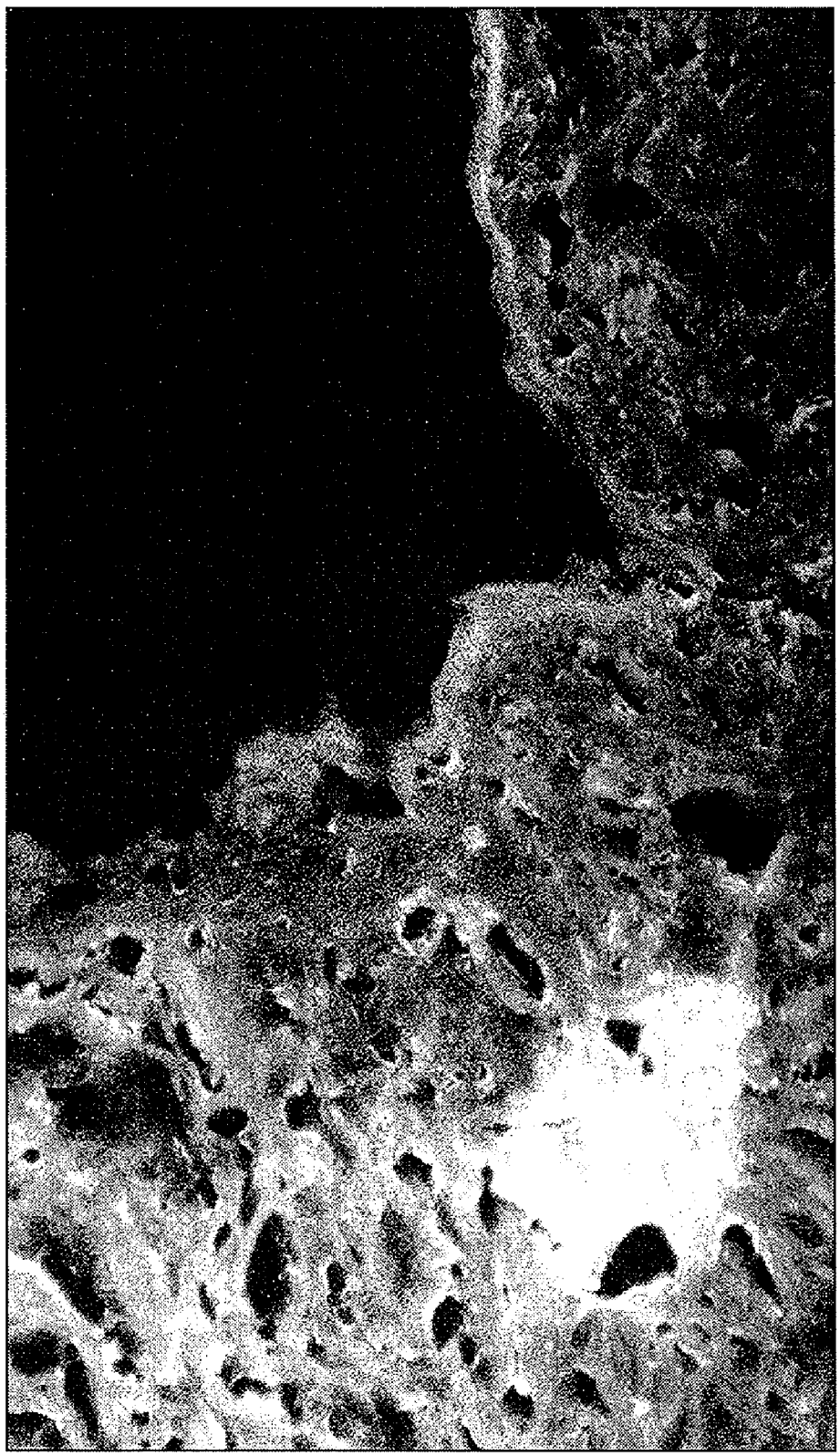
FIG. 4 is a reproduced photograph showing a fluoresceinated (FITC) κ4 mAb bound to human amyloid implanted into a Balb/c mouse. The mAb was injected into the thigh of the mouse. The amyloidoma was excised 72 hours post injection and viewed using an epifluorescence microscope (20× magnification).

In Vivo Studies of Anti-IgLC Subgroups 0.1 mg of one of three antibodies—κ1, κ4, or λ8, identified above—was injected into the thigh of a mouse into which amyloid had been introduced in the form of an amyloidoma as described above. The κ1 and κ4 reagents resulted in the complete removal by the host of most amyloid fibril species tested within 7 days (as little as 4 days for certain sources of amyloid). FIG. 4 shows fluoresceinated κ4 mAb binding to human amyloid.

The λ8 reagent, which is reactive in certain instances in both in vitro studies (above), increased the resolution of amyloidomas by up to about 10% in in vivo experiments.

EXAMPLE 6

In Vivo Studies of Anti-IgLC Subgroups

Human amyloid was isolated from a patient with inflammation-associated, AA-amyloid and prepared for injection into Balb/C mice by repeated sonication and grinding in order to permit its injection into the mouse (see Example 1). Immediately after the injection of 100 mg of human AA-amyloid extract, the mice were treated with 100 μg of κ4 mAb, anti-AA mAb, no mAb and non-specific control mAb (anti-free κ). Complete resolution of the material was observed with 48 hours in the animals that had been treated with the κ4 and anti-AA mAbs. In contrast, the control animals had a large mass of amyloid remaining at the site of injection.

EXAMPLE 7

Production of Specific Anti-Amyloid Fibril mAbs

Synthetic amyloid fibrils were prepared in vitro and used as an immunogen in mice to produce a first generation of anti-amyloid fibril mAbs. Briefly, recombinant λ6-light chain, variable region peptides were produced, isolated and purified using a bacterial expression system and standard protein purification techniques. Synthetic fibrils were prepared from these peptides by extended periods of agitation in solution as described, for example, in Wall et al., "In vitro Immunoglobulin Light Chain Fibrillogenesis," METHODS IN ENZYMOLOGY, Vol. 309 (In Press), which is incorporated herein by reference in its entirety. Fibrils were concentrated by centrifugation at 17,000×g for 20 minutes at room temperature.

The concentrated fibrils were then used to immunize Balb/c mice over a period of several weeks. Monoclonal cell lines secreting anti-fibril antibodies were produced using standard hybridoma techniques. The resultant antibodies have demonstrable anti-fibril activity based upon ELISA assays, described in Example 3. These antibodies reacted with 99% of all human IgLC amyloid extracts tested to date irrespective of the nature of the isotype or subgroup of the precursor protein when tested by ELISA. Similarly, the antibodies reacted in an ELISA format with isolated murine AA-amyloid and synthetic fibrils composed of a peptide derived from the Alzheimer's protein Aβ [Aβ(25-35)].

It should be understood that the foregoing discussion and examples merely present a detailed description of certain preferred embodiments. It therefore should be apparent to those of ordinary skill in the art that various modifications and equivalents can be made without departing from the spirit and scope of the invention. All references, articles and patents identified above are herein incorporated by reference in their entirety.

What is claimed is:

1. A method of treating an amyloid deposition disease in a patient comprising administering to the patient at least one antibody or immunoglobulin polypeptide or fragment thereof which binds to human IgLC amyloid fibrils in an amount effective to enhance the cellular immune response of said patient to remove disease associated amyloid fibril deposits from said patient.

2. The method of claim 1, wherein the antibody or immunoglobulin polypeptide or fragment thereof opsonizes said amyloid fibrils and induces removal of amyloid fibril deposits.

3. The method of claim 1, wherein the antibody or immunoglobulin polypeptide or fragment thereof is a monoclonal antibody or fragment thereof.

4. The method of claim 3, wherein the monoclonal antibody is selected from the group consisting of a humanized antibody, a chimeric antibody and a completely human antibody.

5. The method of claim 3, wherein the monoclonal antibody is selected from the group consisting of κ1 (57-8H12), κ4 (11-1F4), λ8 (31-8C7) and combinations thereof.

6. The method of claim 3, wherein the monoclonal antibody is selected from the group consisting of κ1 (57-8H12), κ4 (11-1F4), λ8 (31-8C7) and combinations thereof or a humanized or chimeric version of said monoclonal antibodies.

7. The method of claim 6, wherein the monoclonal antibody is selected from the group consisting of a humanized antibody or a chimeric antibody.

8. The method of claim 1, wherein the antibody is a labeled antibody.

9. The method of claim 1, wherein the antibody or the immunoglobulin polypeptide or fragment thereof has been raised against an immunoglobulin light-chain.

10. The method of claim 1, wherein the antibody or the immunoglobulin polypeptide or fragment thereof has been raised against synthetic amyloid fibrils.

11. The method of claim 1, wherein the antibody or immunoglobulin polypeptide fragment is selected from the group consisting of a Fv fragment, Fab fragment, F(ab') fragment, F(ab')$_2$ fragment and ScFv fragment.

12. The method of claim 1, wherein the antibody or the immunoglobulin polypeptide or fragment is a single chain antibody.

13. The method of claim 1, wherein the antibody or the immunoglobulin polypeptide or fragment has cross-isotype reactivity.

14. The method of claim 1, wherein the antibody or the immunoglobulin polypeptide or fragment is contained in a pharmaceutical composition further comprising a carrier.

* * * * *